United States Patent
Castrale et al.

(10) Patent No.: US 9,138,339 B2
(45) Date of Patent: Sep. 22, 2015

(54) TOOL GRIPPER

(76) Inventors: Laura Castrale, Dalton, MA (US);
Rebecca Smith, Pittsfield, MA (US);
Todd Volkman, Richmond, MA (US)

(*) Notice: Subject to any disclaimer, the term of this patent is extended or adjusted under 35 U.S.C. 154(b) by 664 days.

(21) Appl. No.: 11/548,173

(22) Filed: Oct. 10, 2006

(65) Prior Publication Data

US 2008/0083306 A1    Apr. 10, 2008

(51) Int. Cl.
*B25G 1/00* (2006.01)
*A61F 4/00* (2006.01)

(52) U.S. Cl.
CPC . *A61F 4/00* (2013.01); *Y10T 16/469* (2015.01)

(58) Field of Classification Search
USPC .............. 16/422, 428, 429, 405, 406; 81/492, 81/3.35; 473/300
See application file for complete search history.

(56) References Cited

U.S. PATENT DOCUMENTS

| | | | | |
|---|---|---|---|---|
| 584,220 A * | 6/1897 | Gunsaul | ...................... | 74/551.9 |
| 1,555,373 A * | 9/1925 | Iden | ............... | 473/610 |
| 4,135,677 A * | 1/1979 | Warczak | .................. | 242/571.1 |
| 4,389,777 A * | 6/1983 | Landsberger | .................. | 30/324 |
| 4,447,912 A * | 5/1984 | Morrow | ............... | 2/159 |
| 4,509,228 A * | 4/1985 | Landsberger | .................. | 16/426 |
| 4,606,484 A * | 8/1986 | Winter et al. | ................. | 224/218 |
| 4,633,552 A * | 1/1987 | Eriksson | .................... | 407/29.15 |
| 4,683,610 A * | 8/1987 | Richards et al. | ................ | 16/429 |
| 4,834,382 A * | 5/1989 | Spector | ........................ | 473/603 |
| 5,085,214 A * | 2/1992 | Barrett | ............................ | 5/648 |
| 5,090,758 A * | 2/1992 | Lord | ........................... | 294/98.1 |
| 5,193,246 A * | 3/1993 | Huang | ........................... | 16/421 |
| 5,355,552 A * | 10/1994 | Huang | ........................... | 16/421 |
| 5,445,342 A * | 8/1995 | Miller et al. | ............... | 242/571.2 |
| 5,509,687 A * | 4/1996 | Thorndike | ................ | 280/766.1 |
| 5,713,104 A * | 2/1998 | Giampaolo, Jr. | ............... | 16/422 |
| 5,846,145 A * | 12/1998 | Tinlin | ......................... | 473/550 |
| 5,853,210 A * | 12/1998 | Robinson | ....................... | 294/25 |
| 5,860,190 A * | 1/1999 | Cano | ........................... | 16/422 |
| 6,079,662 A * | 6/2000 | Miller et al. | ............... | 242/571.2 |
| 6,148,482 A * | 11/2000 | Maraman, Jr. | .................. | 16/421 |
| 6,382,576 B1 * | 5/2002 | Heimbrock | ................ | 248/227.3 |
| 6,637,617 B2 * | 10/2003 | Eisenbraun et al. | .......... | 220/720 |
| 6,648,535 B2 * | 11/2003 | Ferrara, Jr. | ........................ | 401/6 |
| 6,832,413 B1 * | 12/2004 | Applewhite et al. | ............ | 16/430 |
| 7,004,655 B2 * | 2/2006 | Ferrara | ............................ | 401/6 |
| 7,269,875 B1 * | 9/2007 | Grimes | ......................... | 15/119.2 |
| 7,407,444 B2 * | 8/2008 | Cera | ............................ | 473/300 |
| 2003/0029002 A1 * | 2/2003 | Willat | .............................. | 16/430 |
| 2004/0090075 A1 * | 5/2004 | Bushman | ................... | 294/119.3 |
| 2005/0043110 A1 * | 2/2005 | Lindsey | ......................... | 473/300 |
| 2005/0186014 A1 * | 8/2005 | Hohlbein et al. | .............. | 401/123 |
| 2006/0025711 A1 * | 2/2006 | Bell et al. | ......................... | 602/21 |
| 2007/0027411 A1 * | 2/2007 | Ella et al. | .......................... | 601/7 |
| 2008/0083306 A1 | 4/2008 | Castrale et al. | | |
| 2009/0007359 A1 * | 1/2009 | Hohlbein et al. | ............ | 15/167.1 |

* cited by examiner

*Primary Examiner* — Robert J Sandy
*Assistant Examiner* — Rowland Do
(74) *Attorney, Agent, or Firm* — Fish & Richardson P.C.

(57) ABSTRACT

An apparatus for gripping a tool shaft includes a tubular handle having an opening for receiving a tool shaft; an air bladder disposed within the tubular handle for selectively constricting the opening; and a valve in pneumatic communication with the air bladder for inflating the air bladder, thereby causing the air bladder to grip a tool shaft inserted therethrough.

19 Claims, 10 Drawing Sheets

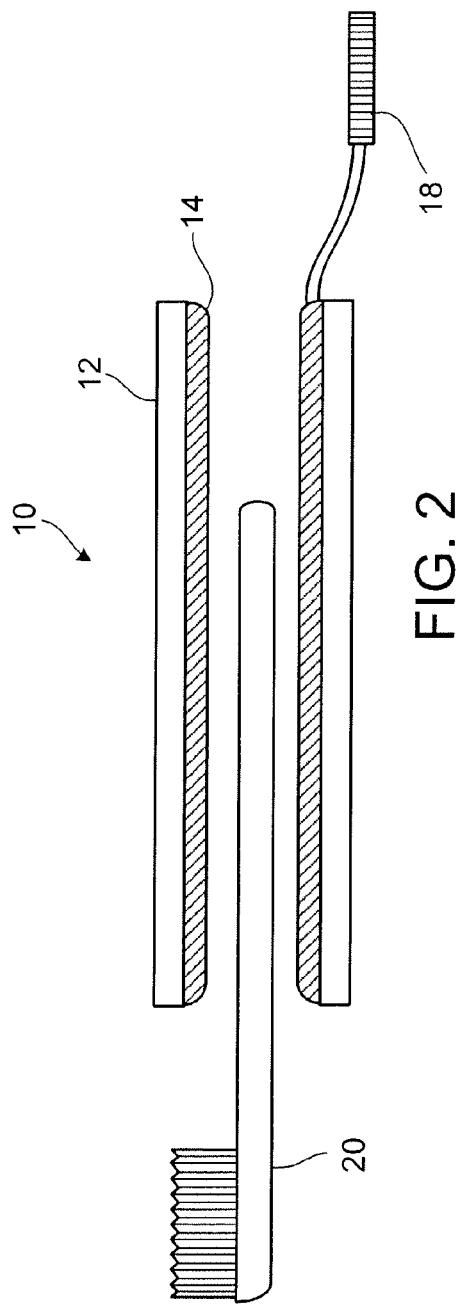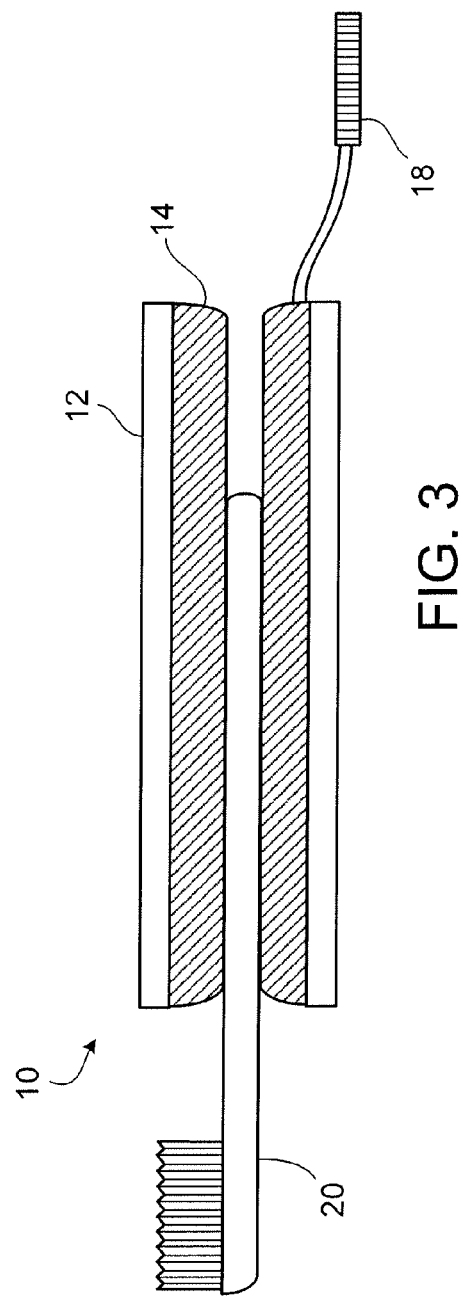

TOOL GRIPPER

FIELD OF DISCLOSURE

This disclosure relates to devices for improving handicapped accessibility, and in particular, to devices for gripping tools.

BACKGROUND

Many people are afflicted with conditions that adversely affect their ability to grip objects. Such people often have difficulty using tools that have small cross-sectional areas. Examples of such tools one encounters in everyday life include toothbrushes, cutlery, writing implements, backscratchers, and the like.

A known method for overcoming difficulty gripping such tools is to simply use tools that have been customized with a larger handle, or shaft. For example, one can purchase knives, forks, and spoons whose shafts have been enlarged to accommodate those with gripping difficulties.

Many common tools, particularly kitchen tools, such as vegetable peelers, or bottle-openers, are made with enlarged handles to facilitate gripping. However, many other common tools are manufactured only with handles that are more difficult to grip. For example, it is difficult to find cutlery with enlarged handles. And even if one did find such cutlery, it would be inconvenient to carry that cutlery wherever one dined.

SUMMARY

In one aspect, the invention features an apparatus for gripping a tool shaft, the apparatus including a tubular handle having an opening for receiving a tool shaft; an air bladder disposed within the tubular handle for selectively constricting the opening; and a valve in pneumatic communication with the air bladder for inflating the air bladder, thereby causing the air bladder to grip a tool shaft inserted therethrough.

In some embodiments, the air bladder includes first and second lobes diametrically opposed to each other within the tubular handle.

In other embodiments, the air bladder includes a plurality of circumferentially disposed within the tubular handle.

In yet other embodiments, the air bladder includes an annular bladder.

Additional embodiments include those in which the handle includes a constricted waist portion.

Yet other embodiments include those having a circumferential ridge protruding from an inner surface of the tubular handle, the ridge being disposed to contact the air bladder when the air bladder is at least partially inflated.

In some embodiments, the air bladder includes a folded inner tube having a valve end and two open ends.

Additional embodiments include those that also include an annular clamp for clamping the open ends to the tubular handle.

Yet other embodiments include those in which the air bladder includes a plurality of lobes axially displaced from each other along an axis of the handle.

Some embodiments also include a docking station having a receptacle sized to receive the tubular handle, and a platform to support the tool shaft for insertion into the handle, the platform being disposed to be adjacent to the opening when the tubular handle is in the receptacle.

Embodiments also include those in which the handle has a diameter of between about one inch and two inches, and those in which the handle has a length of between about two inches and four inches, and those in which the handle has a length of between about four inches to six inches.

In another aspect, the invention features a method for gripping a tool shaft. The method includes deflating a bladder, thereby increasing a cross-sectional area of the aperture; inserting tool shaft into an aperture; and inflating a bladder, thereby reducing the cross-sectional area of the aperture.

In another aspect, the invention features an apparatus for gripping a tool shaft. Such an apparatus includes a handle having an opening for receiving a tool shaft; and a gripper disposed within the opening for gripping a tool shaft inserted therethrough.

In some embodiments, the gripper includes an air bladder that transitions between a first state, in which the air bladder constricts the opening, and a second state, in which the air bladder dilates the opening.

In other embodiments, the gripper includes at least a first barrier disposed transversely across the tool shaft, the first barrier having a first opening sized to receive the tool shaft; and a second barrier disposed transversely across the tool shaft and axially displaced from the first barrier, the second barrier having an opening sized for receiving the tool shaft, the second opening being collinear with the first opening. Among these are the embodiments in which the first barrier includes a polycarbonate film.

These and other features of the invention will be apparent from the following detailed description and the figures, in which:

BRIEF DESCRIPTION OF THE DRAWINGS

FIGS. 2 and 3 show the gripper of FIG. 1 in each of two states;

DETAILED DESCRIPTION

Figure 1:
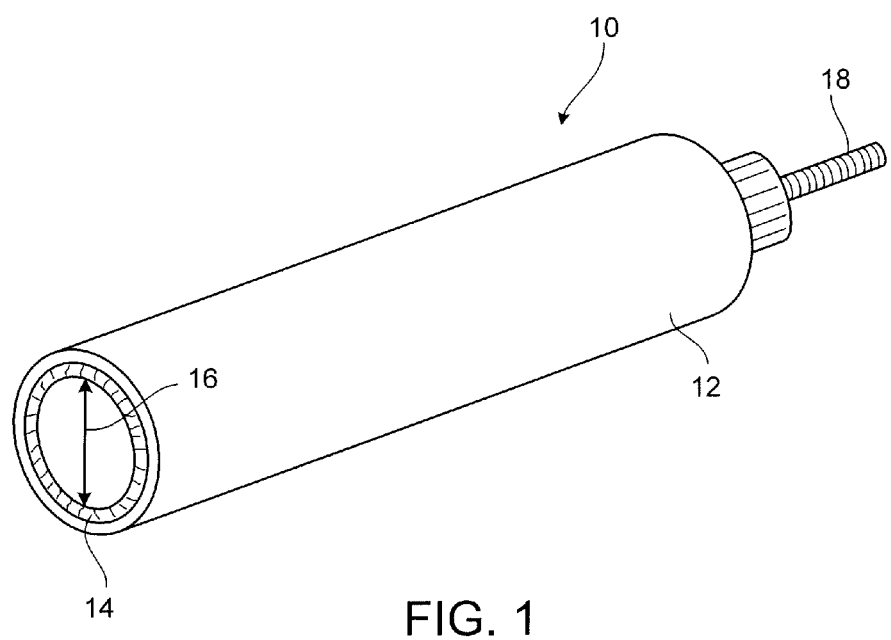
FIG. 1 is an isometric view of a gripper.

FIG. 1 shows a gripper 10 having a handle 12 that defines a longitudinal direction, a radial direction, and a circumferential direction. An inflatable air bladder 14 within the handle 12 defines a variable inner diameter 16. A valve 18 in pneumatic communication with the air bladder 14 allows one to selectively inflate and deflate the bladder 14, thereby permitting one to change the inner diameter 16.

To use the gripper 10, one deflates the bladder 14 until the inner diameter is large enough to enable a shaft 20 to be easily inserted therein. Then, one inserts the shaft 20 through the tube, as shown in cross section in FIG. 2. Finally, as shown in FIG. 3, one inflates the bladder 14 until the inner diameter is small enough so that the bladder 14 grips the shaft 20.

The gripper 10 shown in FIGS. 1-3 is particularly advantageous because the bladder 14 conforms to the shape of the shaft 20. This allows the gripper 10 to effectively grip shafts 20 having irregular shapes. Such shafts 20 are common in cutlery, or in ergonomically designed toothbrushes.

An additional advantage of a gripper 10 that uses a bladder 14 arises from the extended contact area between the bladder 14 and the shaft 20 in the longitudinal direction. This extended contact area enables the gripper 10 to effectively resist forces in the longitudinal direction.

Figure 4:
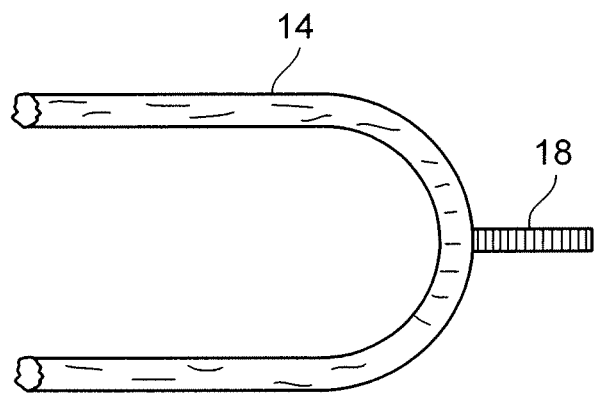
FIGS. 4-6 show stages in the assembly of a gripper like that shown in FIG. 1.

A gripper 10 like that shown in FIGS. 1-3 can be constructed by cutting an inner tube having a vale 18, as shown in FIG. 4, to create two open ends with the valve 18 approximately midway between the open ends. The inner tube can be, for example, the inner tube of a bicycle.

Figure 5:
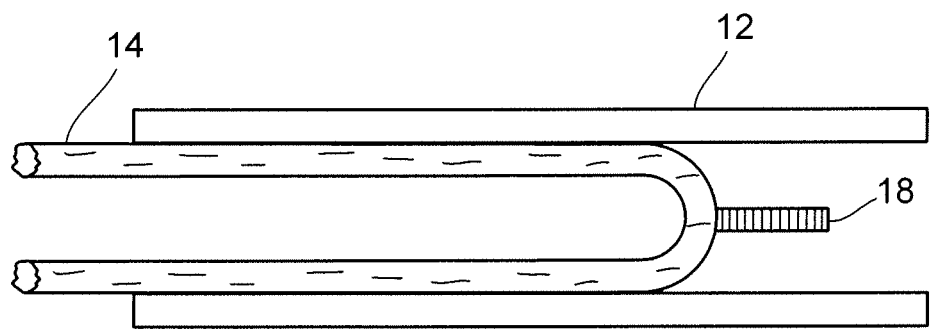
Figure 6:
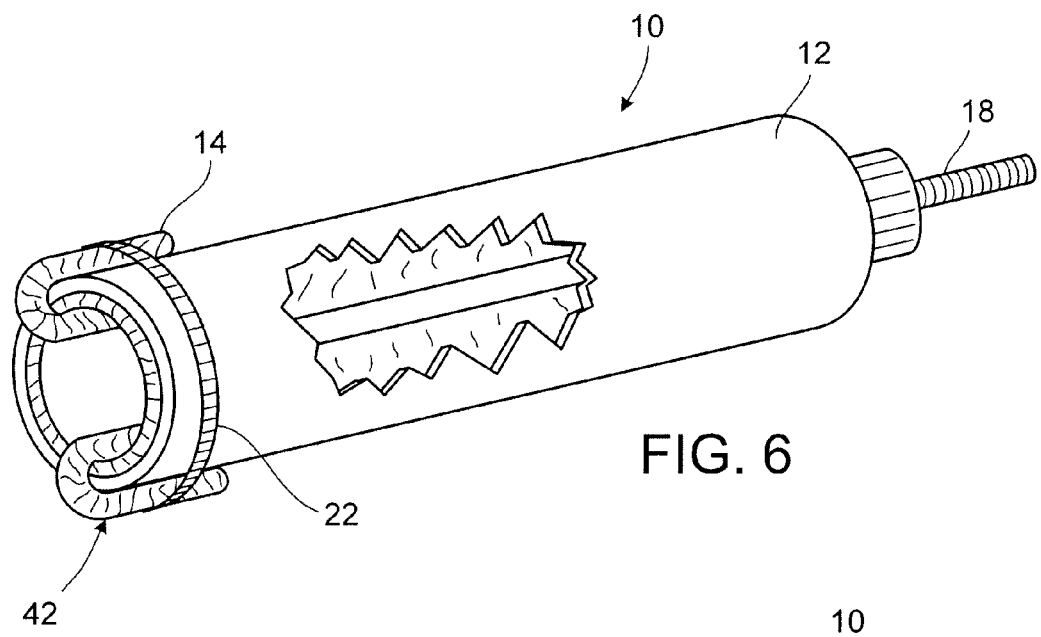

The inner tube is then folded over so that the open ends almost meet. Then, the folded inner tube 42 is inserted, with its valve 18 leading the way, into a tube that functions as a handle 12, as shown in FIG. 5. When the inner tube is inserted far enough so that the valve 18 protrudes out a first end of the tube, the open ends of the inner tube are folded over a second end of the tube and secured by an annular clamp 22 to prevent air from leaking out the open ends. This final configuration of a folded inner tube 42 is shown in FIG. 6.

Figure 7:
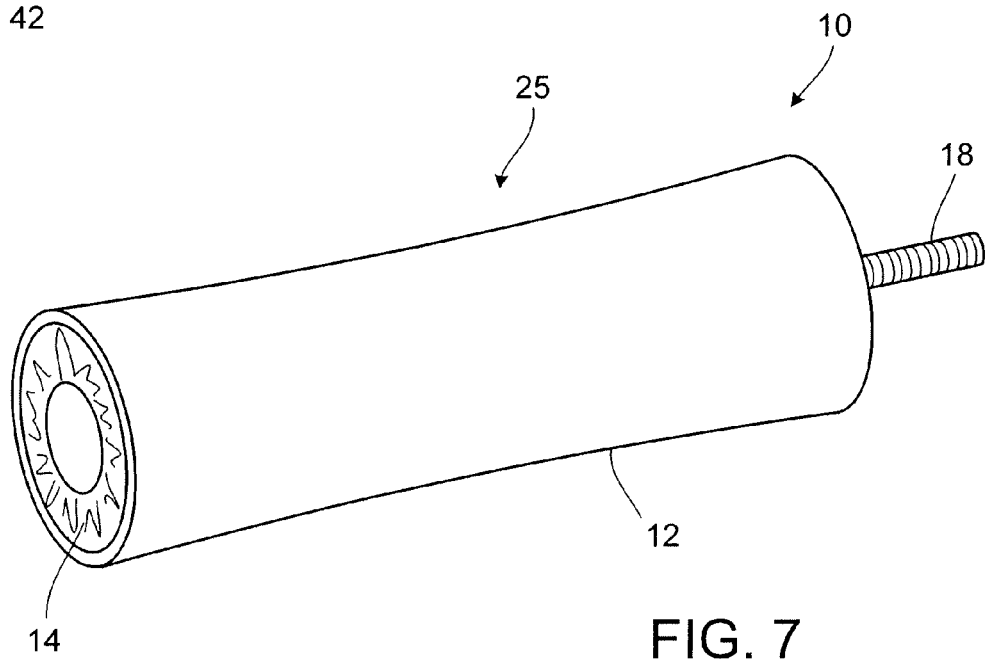
FIG. 7 shows a gripper having a handle with a waist.

A suitable tube is a PVC tube having an outer diameter sized to accommodate a user's hand. This diameter would vary depending on the size of the user's hand. The tube need not be cylindrical as shown in FIGS. 1-3, but can also have a constricted waist 25, as shown in FIG. 7. For some applications, a constricted waist 25 is useful because it enables the hand to resist forces acting along the axis of the tube.

Because PVC is somewhat slippery, it may be useful in some embodiments to cover, or partially cover, the tube with an outer friction layer having a high friction coefficient. A suitable friction layer can be made by wrapping the tube with tape, or by attaching a suitable material with an adhesive.

An annular clamp can be made of one or more elastic bands, a hose clamp, an O-ring, or any similar structure.

A pump can be used to inflate the bladder 14. The pump could be manually operated, either by a foot pedal or by a handle. Or the pump could be a battery-operated electric pump.

Deflation of the bladder 14 only requires pressing the spring-loaded pin on the valve 18. In some embodiments, it is useful to provide an actuator to press the pin on the valve 18. Such an actuator could be configured to depress the pin when a button is pressed.

In some cases, a more convenient valve 18 may be one that is inflated by the user's own lung power. Such valves are common in, for example, air mattresses or pillows. The use of such valves avoids the need to provide a pump.

Figure 8:
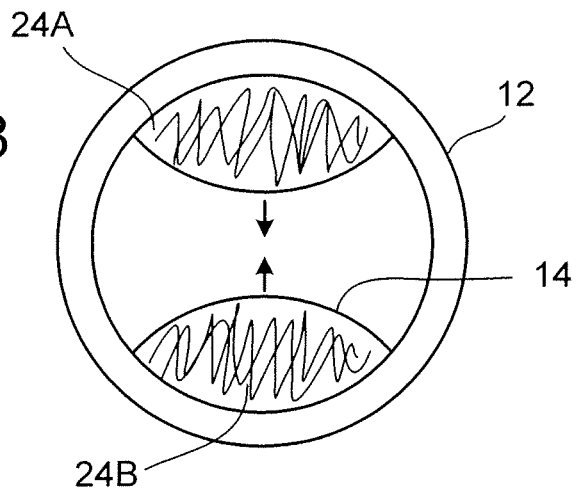
FIGS. 8 and 9 are cross-sections of a gripper having bladders with two and three lobes respectively.

In cross-section, a gripper 10 constructed as described above results in a bi-lobal bladder 14 having two lobes 24A-B, each of which has a radial dimension that varies with circumferential angle. Each lobe 24A-B defines a grip vector that extends between the center of the tube and the maximum radial excursion of that lobe 24A-B, as shown in FIG. 8. Each lobe 24A-B effectively resists forces parallel to its grip vector. However, since the two grip vectors are parallel, the configuration shown in FIG. 8 may encounter difficulty resisting forces perpendicular to the two grip vectors.

To overcome the foregoing disadvantage, alternative embodiments of the gripper 10 feature a bladder 14 that forms more than two lobes. Such bladders define grip vectors that are no longer parallel to each other, and thereby more effectively resist forces acting in a variety of directions.

Figure 9:
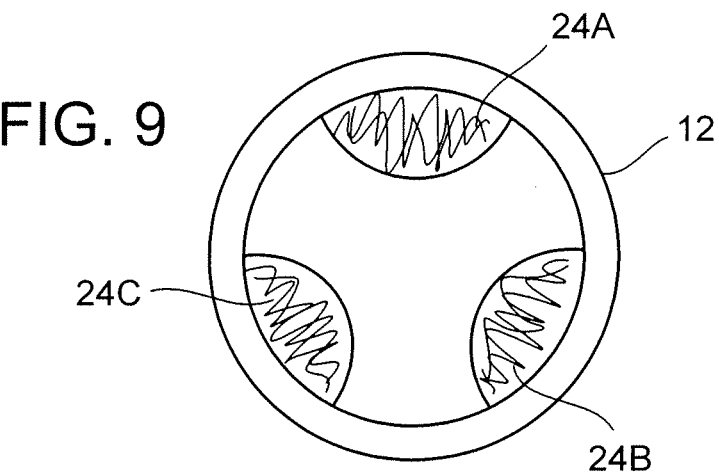
Figure 10:
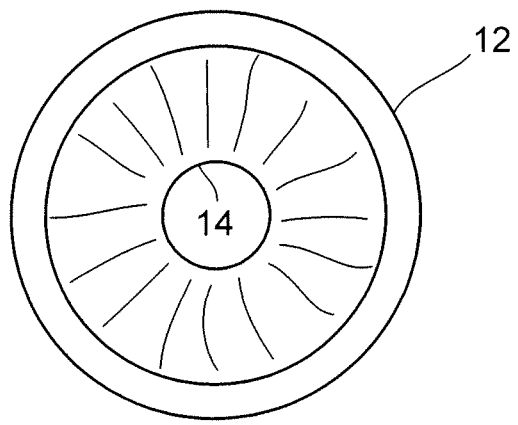
FIG. 10 is a cross-section of a gripper having an annular bladder.

FIG. 9 shows a tri-lobal bladder 14 having lobes 24A-C that define grip vectors separated by 120 degrees. Such a bladder 14 significantly enhances gripping ability. Bladders having four or more lobes further enhance gripping ability. In some embodiments, the bladder 14 is annular, as shown in FIG. 10. The annual bladder 14, which can be viewed as a limiting case of a multi-lobal bladder 14, where the number of lobes effectively becomes infinite, effectively resists forces in any radial direction.

In the case of a multi-lobal bladder 14, the various lobes can be connected by a common manifold so that all lobes inflate and deflate together. However, a bladder 14 can also include distinct compartments that are not in pneumatic communication with each other. In such cases, the different lobes of the bladder 14 can be inflated and deflated independently of each other.

Figure 11:
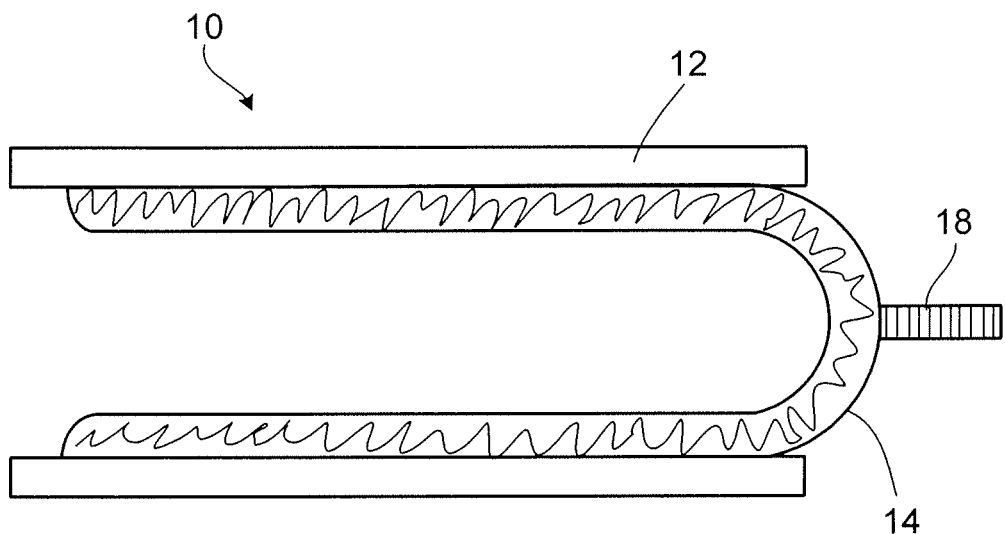
FIG. 11 is a longitudinal section of a gripper.

As shown in FIG. 11, the bladder 14 has a natural tendency to bulge outward near the center of the handle 12. This results in gripping force that varies along the shaft 20, with a maximum force near the center and smaller forces near the ends of the handle 12. As a result, the shaft 20 may pivot in response to an applied torque.

Figure 12:
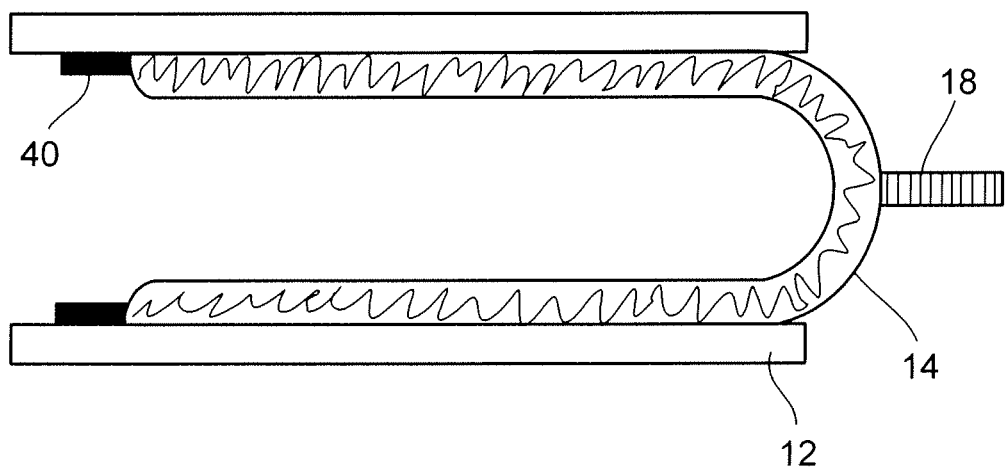
FIG. 12 is a longitudinal section of a gripper having a rib.

To reduce this longitudinal variation in gripping force, it is useful to provide a circumferential ridge 40 at each end of the handle 12, as shown in FIG. 12. Such a ridge protrudes from the inner wall of the handle 12 at a point that is far enough from the ends of the handle 12 so that the bladder 14 rests against the ridge. This changes the boundary condition at the longitudinal ends of the bladder 14, thereby causing the bladder 14 to assume a more uniform profile in the longitudinal direction.

Figure 13:
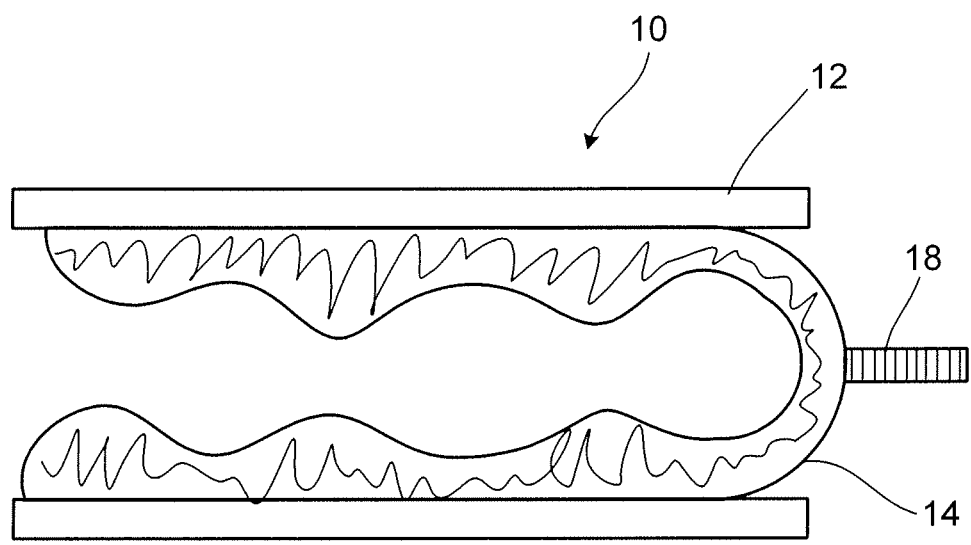
FIG. 13 is a longitudinal section of a gripper having a bladder with axially displaced lobes.

Another way to equalize gripping force along the longitudinal axis of the handle 12 is to provide multiple bladder 14 lobes that are axially disposed relative to each other as shown in FIG. 13. In this case, the lobes can be connected to a common manifold, so that they inflate and deflate together as a unit. Alternatively, the lobes can be separate, so that they deflate and inflate independently of each other.

Figure 15:
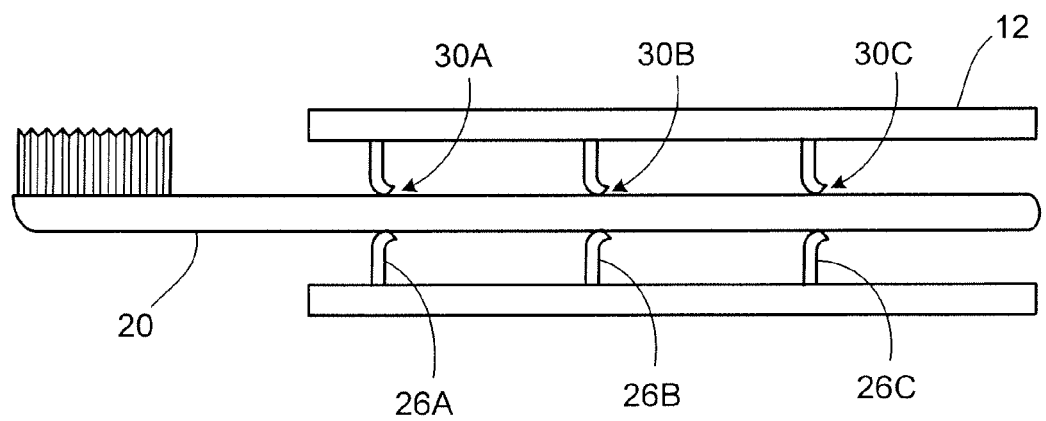
FIG. 15 is a longitudinal views of the gripper of FIG. 14 as it grips a shaft.

Another embodiment of the gripper 10, shown in isometric view in FIG. 15 and in cross section view in FIG. 15, features a handle 12 that defines a longitudinal direction and a radial direction. The handle 12 has a cylindrical interior volume. A number of barriers, e.g. 26A, 26B, 26C, each disposed at a different longitudinal coordinate, extend transversely across the interior volume, effectively dividing the interior volume into a corresponding number of cylindrical chambers. Each disk has a variable opening, e.g. 30A, 30B, 30C, that has a tendency to stay as small as possible. Preferably, the variable openings are arranged along the center of the tube. However, in some embodiments, the variable openings are arranged collinearly.

A suitable barrier is a thin polycarbonate sheet similar to those used as lids for disposable drinking glasses. The variable opening can be formed by cutting a slit in the barrier, or by cutting a pair of intersecting slits. A variable opening of this type, when cut into a polycarbonate film, is similar to the opening commonly used for inserting straws through disposable lids of drinking glasses.

Figure 14:
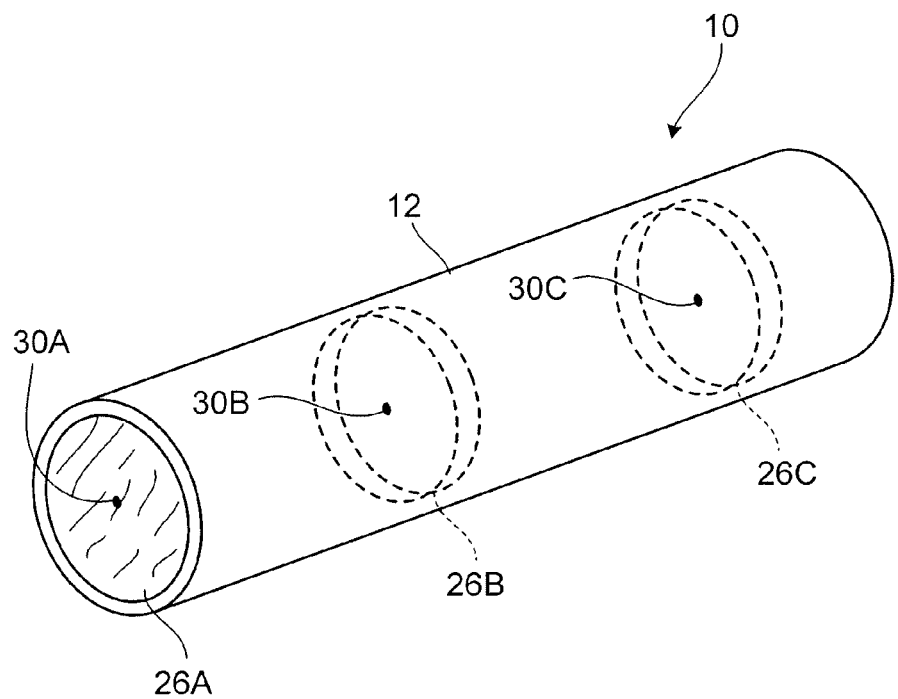
FIG. 14 is an isometric view of another embodiment of the gripper.

To use the gripper 10 shown in FIG. 14, one inserts a shaft 20 through each of the variable openings 30, as shown in FIG. 15. The film immediately surrounding each variable opening then exerts a force that tends to grip the shaft 20.

As the number of barriers increases, the total gripping force increases. As the spacing between barriers increases, the ability to resist external torques on the shaft 20 increases. However, in both cases, the grip becomes more difficult to use because as the number of barriers increases, so too does the frictional force acting on the shaft 20. As a result, the shaft 20 becomes progressively more difficult to push as it extends deeper into the handle 12.

The embodiment shown in FIG. 12 is most effective for shafts that are relatively straight and uniform in cross section. Shafts having irregular shapes or varying cross-sectional areas are more easily gripped with an air bladder 14 as described in connection with the gripper 10 of FIG. 1.

An apparatus as described herein can be used for gripping a variety of objects, including, but not limited to toothbrushes, combs, brushes, and other personal care devices, cutlery, cooking utensils, pencils, pens, and other writing implements, paint brushes, hand tools and the like. The specific dimensions of the tube, as well as on the gripping mechanisms described herein depend on the size of the user's hand and on the nature of what is to be gripped.

Figure 16:
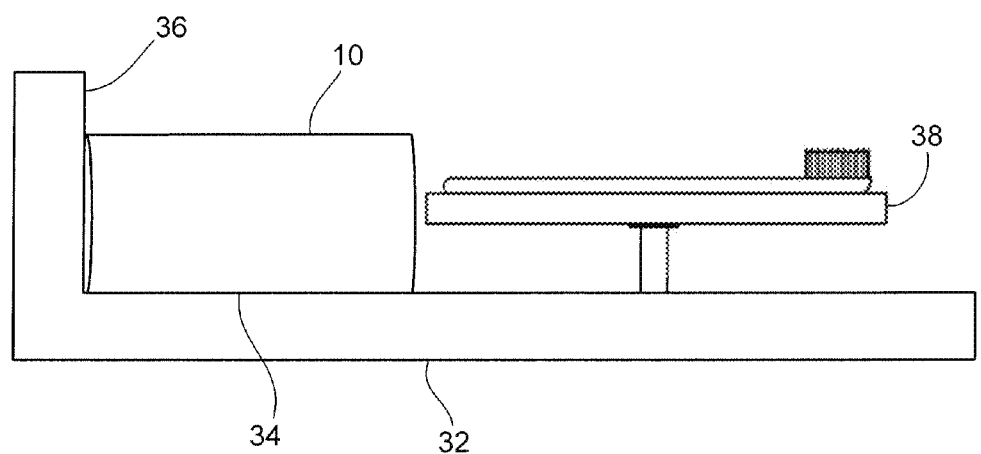
FIG. 16 shows a gripper used with a docking station.
Figure 17:
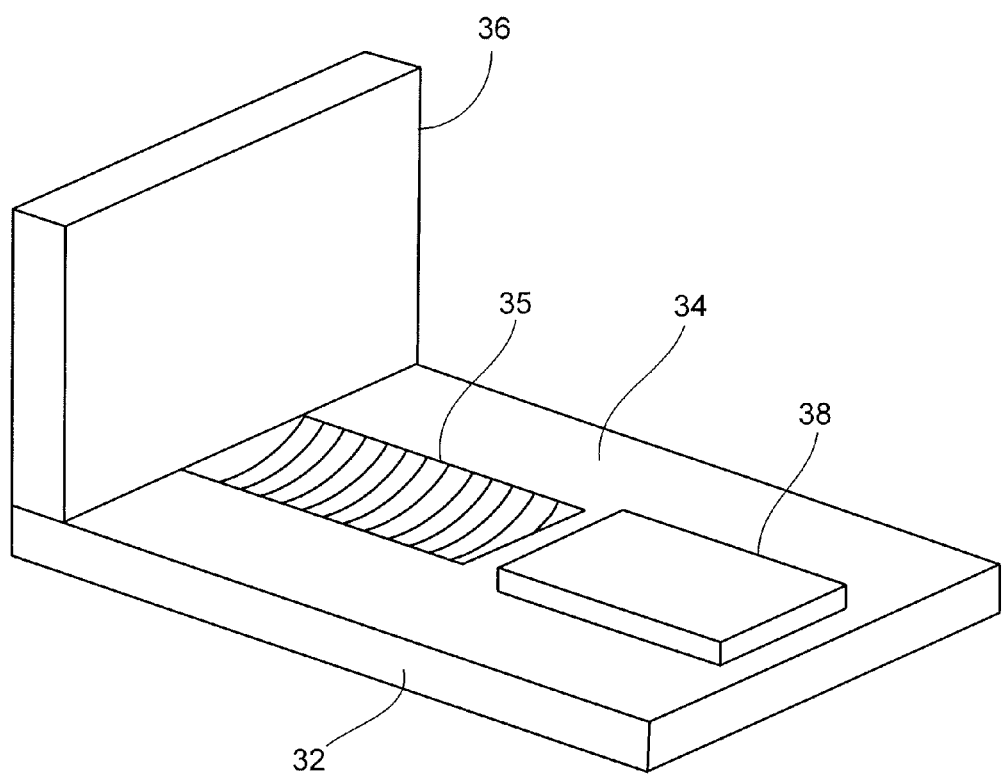
FIG. 17 shows a recess in the docking station.

In many cases, the extend of a user's disability may be such that even picking up the tool to insert it into the grip may be difficult. To accommodate such difficulties, the gripper 10 can be placed in a docking station 32, as shown in FIG. 16, having a dock 34 for receiving the gripper 10 and a back-stop 36 directly behind the receptacle. The dock 34 features a recess 35, best seen in FIG. 17, to secure the gripper 10.

In front of the receptacle, on the other side from the back-stop, is a platform 38 for receiving a tool to be gripped. The platform is positioned to be substantially coplanar with a horizontal plane that bisects the gripper 10 when the gripper 10 is in the dock. As a result, a tool shaft 20 placed on the platform can readily be aligned with the center of the tube by simply rolling it left or right.

To use the docking station, one places the gripper 10 in the dock with its receiving end facing the platform. Then, one aligns the platform with a table on which a tool has been placed. With the platform aligned, one then rolls the tool onto the platform and centers it on the platform relative to the opening on the receiving end of the gripper 10. With the tool now centered, one pushes it through the receiving aperture and into the gripper 10.

The height of the platform 38 depends, to some extent, on the depth of the recess 35. For example, if the recess 35 has a depth of approximately the radius of the gripper 10, then the platform 38 can be coplanar with the dock 34.

Having described an invention, and a preferred embodiment thereof, what we claim as new, and secured by Letters Patent is:

1. An apparatus comprising:
    a structure that encloses an elongated space along an axis, and
    an inflatable bladder that has (a) a flexible outer bladder surface that engages an interior of the structure, (b) a flexible inner bladder surface that encloses a tubular inner space that is within the elongated space and is sized to receive a handle of a handheld tool, and (c) an interior space between the two flexible bladder surfaces to hold a pressurized fluid,
    the inflatable bladder comprising (a) two segments that meet at a fold, (b) a valve that is at an apex of the fold and extends along the axis at a first end of the structure, and (c) two ends of the two segments, the two ends located in the vicinity of a second end of the structure, the fold being located on the inflatable bladder such that the inner surface of the inflatable bladder can engage the handheld tool on the two segments that meet at the fold, the structure that encloses the elongated space being sufficiently rigid to resist expansion of the inflatable bladder.

2. The apparatus of claim 1, wherein the inflatable bladder comprises at least two lobes diametrically opposed to each other across a longitudinal axis of the structure that encloses the elongated space.

3. The apparatus of claim 1, wherein the inflatable air bladder comprises a plurality of lobes circumferentially disposed about the tubular handle axis, within the tubular handle volume.

4. The apparatus of claim 1, wherein the inflatable air bladder comprises an annular bladder extending generally about the tubular handle axis, within the tubular handle volume.

5. The apparatus of claim 1, wherein the structure that encloses the elongated space comprises an outer gripping surface that defines a constricted waist portion.

6. The apparatus of claim 1, wherein the structure that encloses the elongated space includes a circumferential ridge protruding from the inner surface, the ridge being disposed to contact the inflatable bladder when the inflatable bladder is at least partially inflated.

7. The apparatus of claim 6 in which the ridge is proximate to the second end of the structure.

8. The apparatus of claim 1, further comprising an annular clamp disposed in clamping arrangement with the two ends of the folded tube and the structure that encloses the elongated space.

9. The apparatus of claim 1, wherein the inflatable bladder comprises a plurality of lobes axially displaced from each other along a longitudinal axis of the structure that encloses the elongated space.

10. The apparatus of claim 1, further comprising a docking station having
    a receptacle sized to receive the elongated tubular handle, and
    a platform to support the tool shaft for insertion into the opening in the tubular handle, the platform being disposed adjacent to the tubular handle opening when the tubular handle is in the receptacle.

11. The apparatus of claim 1, wherein the structure that encloses the elongated space has a diameter between about one inch and two inches.

12. The apparatus of claim 1, wherein the structure that encloses the elongated space has a length of between about four inches and six inches.

13. The apparatus of claim 12, wherein the apparatus has a length of between about four inches and six inches.

14. A method for using the apparatus claim 1 for gripping a tool shaft, the method comprising: providing the apparatus of claim 1;
    deflating the inflatable air bladder, thereby increasing a cross-sectional area of the tubular handle opening;
    inserting a tool shaft into the aperture defined by the inflatable bladder in deflated state; and
    inflating the inflatable air bladder, thereby constricting the cross-sectional area of the aperture and gripping the tool shaft.

15. The apparatus of claim 1, wherein the valve protrudes beyond the first end of the structure that encloses the elongated space.

16. The apparatus of claim 1 in which the structure comprises all of the length of the apparatus.

17. The apparatus of claim 1 in which the structure provides resistance to the expansion of the inflatable bladder along the full length of the inflatable bladder.

18. The apparatus of claim 1 in which the structure provides resistance to the expansion of the inflatable bladder at all radial positions about an axis of the structure.

19. An apparatus comprising:
a structure that encloses an elongated space along an axis, and
an inflatable bladder that has (a) a flexible outer bladder surface that engages an interior of the structure, (b) a flexible inner bladder surface that encloses a tubular inner space that is within the elongated space and is sized to receive a handle of a handheld tool, and (c) an interior space between the two flexible bladder surfaces to hold a pressurized fluid, the inner bladder surface being reconfigurable between a deflated state in which the tubular inner space is larger than the handle and an inflated state in which the tubular inner space matches the handle,
the structure that encloses the elongated space being sufficiently rigid to resist expansion of the inflatable bladder, the structure comprising at least most of the length of the apparatus,
wherein the structure that encloses the elongated space has a diameter between about one inch and two inches;
the structure that encloses the elongated space has a length of between about four inches and six inches;
the structure comprises all of the length of the apparatus;
the structure provides resistance to the expansion of the inflatable bladder along the full length of the inflatable bladder;
the structure provides resistance to the expansion of the inflatable bladder at all radial positions about an axis of the structure; and
the inflatable bladder comprises (a) two segments that meet at a fold, (b) a valve that is at an apex of the fold and extends along the axis at a first end of the structure, and (c) two ends of the two segments, the two ends located in the vicinity of a second end of the structure, the fold being located on the inflatable bladder such that the inner surface of the inflatable bladder can engage the handheld tool on the two sides that meet at the fold.

* * * * *

UNITED STATES PATENT AND TRADEMARK OFFICE
CERTIFICATE OF CORRECTION

| | | |
|---|---|---|
| PATENT NO. | : 9,138,339 B2 | Page 1 of 1 |
| APPLICATION NO. | : 11/548173 | |
| DATED | : September 22, 2015 | |
| INVENTOR(S) | : Laura Castrale, Rebecca Smith and Todd Volkman | |

It is certified that error appears in the above-identified patent and that said Letters Patent is hereby corrected as shown below:

In the claims

Column 6, Line 47, In Claim 13, before "claim 1" insert -- of --.

Signed and Sealed this
Twenty-third Day of February, 2016

Michelle K. Lee
*Director of the United States Patent and Trademark Office*